United States Patent [19]

Clingman, Jr.

[11] 4,125,123
[45] Nov. 14, 1978

[54] METHODS OF AND MEANS FOR ACCURATELY MEASURING THE CALORIFIC VALUE OF COMBUSTIBLE GASES

[75] Inventor: William H. Clingman, Jr., Dallas, Tex.

[73] Assignee: Precision Machine Products, Inc., Dallas, Tex.

[21] Appl. No.: 824,031

[22] Filed: Aug. 12, 1977

Related U.S. Application Data

[62] Division of Ser. No. 682,578, May 3, 1976, Pat. No. 4,062,236.

[51] Int. Cl.² ............................................. G01N 25/30
[52] U.S. Cl. ..................................... 137/80; 137/486; 73/190 CV
[58] Field of Search .............. 137/486, 487.5, 80, 137/79; 73/190 CV, 190 R

[56] References Cited

U.S. PATENT DOCUMENTS

| 3,393,562 | 7/1968 | Breedlove | 73/190 CV |
| 4,042,173 | 8/1977 | Boyer et al. | 137/486 X |

*Primary Examiner*—Alan Cohan
*Attorney, Agent, or Firm*—Joseph H. Schley; Thomas L. Cantrell

[57] ABSTRACT

Method of and means for accurately measuring the calorific value of combustible gases wherein a mixture of combustible gas and combustion-supporting gas is burned in a pair of flames, the temperatures of the burned gases in both flames being monitored and the volume ratios of the combustion-supporting gas to the combustible gas fed to both burners being adjusted so as to maintain the average of said temperatures at substantially maximum; the volume ratio of said gases which produces said maximum average temperatures varying substantially directly with the calorific value of said combustible gas; the aforesaid calorific value being proportional to said volume ratio of said gases which maximizes said average temperatures; the flow rates of said gases being measured by a single flow sensing system, preferably, of the turbine flowmeter types, or the volumetric flow rate of said combustion-supporting gas being maintained at a constant value while the volumetric flow rate of said combustible gas is being measured; said calorific value measuring method and means being unaffected by ambient temperature and other varying environmental factors.

1 Claim, 3 Drawing Figures

METHODS OF AND MEANS FOR ACCURATELY MEASURING THE CALORIFIC VALUE OF COMBUSTIBLE GASES

This application is a division of application Ser. No. 682,578, filed May 3, 1976, now U.S. Pat. No. 4,062,236, which is an improvement of the William H. Clingman, Jr. U.S. Pat. No. 3,777,562, issued Dec. 11, 1973.

SUMMARY OF THE INVENTION

As used herein, the word "air" or the words "dry air" include any combustion-supporting or oxygen containing gas, and the word "gas" includes any combustible gas or gaseous mixture containing one or more combustible gases.

The basic method of this invention includes the following steps:

(1) combustible gas is mixed with dry air or other combustion-supporting or oxygen-containing gas;

(2) mixture is burned in a pair of flames;

(3) temperatures of these flames or burned gases are monitored;

(4) volume ratio of the gases is adjusted so as to maintain the average of said temperatures at substantially maximum;

(5) said volume ratio of said gases which produces said maximum average temperature is measured and is substantially proportional to the calorific value.

The flow rates of these gases may be measured by a single flow sensing system which is, preferably, of the turbine flowmeter type whereby a measured ratio of said flow rates is obtained and is substantially proportional to the calorific value. Alternately, the volumetric flow rate of the air or combustion-supporting gas may be regulated at a constant value with the volumetric flow rate of the combustible gas being measured.

In accordance with the present invention, the employment of a single flow sensing system is of great advantage. At the pressures and flow rates typically involved in a calorific measuring device, turbine meters have been found to be superior to other types of flowmeters. But because of inevitable manufacturing variances between flowmeters, it is difficult to find a "matched pair" suitable for use together in a single apparatus, thus necessitating complex compensating circuits in the electric signal processing equipment which monitors the flowmeters. When all flow measurements are made with a single flowmeter, as in the present invention, the need for matching flowmeters or compensating for their mismatch is avoided.

The aforesaid measured volume ratio is referred to hereinafter as "critical combustion ratio" and may be defined as that volume ratio of the gases which produces maximum average flame temperatures when said gases are premixed and burned. It has been found that the critical combustion ratio of these gases varies substantially directly with the calorific value of the combustible gas and that a very accurate indication of calorific value can be obtained by measuring said critical combustion ratio.

As set forth in the aforesaid Clingman, Jr. patent, it is well-known that the adiabatic temperature of a flame that is produced by burning a mixture of combustible and combustion-supporting gases is a function only of the initial temperature, pressure and chemical composition of the mixture and that said adiabatic temperature is reached in the combustion zone of the flame only if there are no heat losses from the burning gases. Also, if the ratio of combustion-supporting gas to combustible gas is varied in the initial mixture, the adiabatic flame temperature varies and a critical ratio between the gases exists at which said adiabatic flame temperature is at maximum. If the initial mixture contains less combustion-supporting gas than required to achieve this critical ratio, the adiabatic flame temperature is lower and this is generally due to insufficient oxygen being present to achieve complete combustion whereby less heat is released. In the event that the initial mixture contains combustion-supporting gas in excess of that required to achieve the critical ratio, the adiabatic flame temperature is again lower and is generally due to the necessity of heating such excess. Thus, the critical ratio between the gases is equal to the critical combustion ratio defined hereinbefore.

Objects of the invention include the provision of an improved method of and means for measuring the calorific value of combustible gases which are not dependent upon measuring the amount of heat released in combustion, which utilize a single flow sensing system, preferably, of the turbine flowmeter type, to measure the flow rates of both combustible and combustion-supporting gases or said flow rate of said combustible gas may be so measured while said flow rate of said combustion-supporting gas is maintained at a constant value, which are not affected by the turbine calibration factor of the sensing system, which are relatively simple, which are capable of continuous simple operation, and which are not affected by ambient temperature and other varying environmental factors.

DESCRIPTION OF A PREFERRED EMBODIMENT

Figure 1:
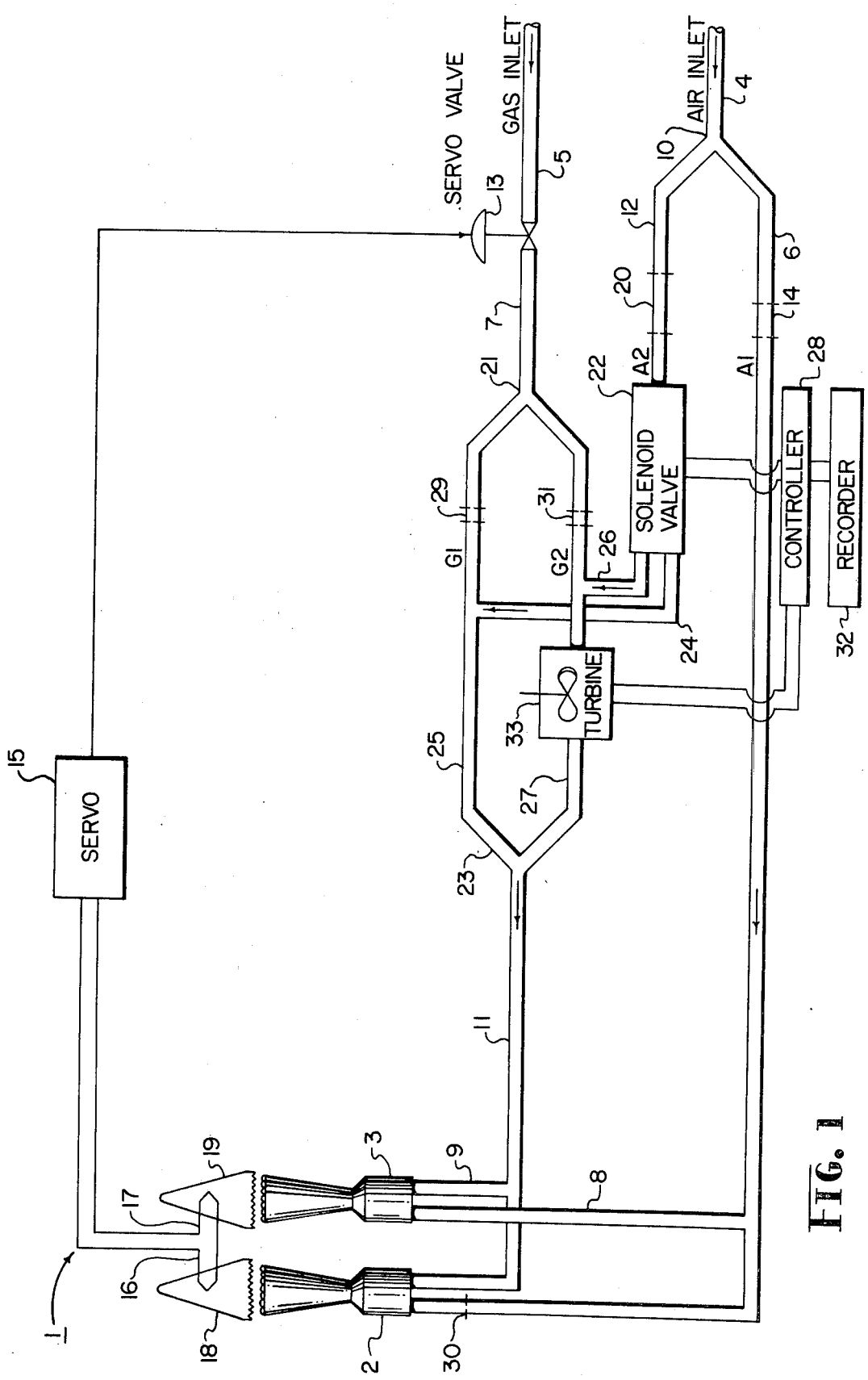
FIG. 1 is a diagrammatic view illustrating an apparatus for carrying out one of the methods of this invention.

In the drawings, the numeral 1 schematically designates an apparatus for accurately measuring the critical combustion ratio or caloric value of a combustible gas which comprises a pair of burners 2, 3 respectively communicating with an air inlet 4 and a combustible gas inlet 5. A fluid conductor or main air line 6 connects the base of the burner 2 to the air inlet 4, and said burner base communicates with the gas inlet 5 through a fluid conductor or main gas line 7. The main air and gas lines 6, 7 are connected to the base of the burner 3 by branch fluid conductors or lines 8, 9, respectively, said gas line 7 having an egress portion 11 of extended length. It is noted that the base of each burner is so constructed that it functions as a mixing chamber for the gas and air conducted thereto by the lines 6, 7, 8, 9. As will be described more fully hereinafter, a forked or Y-shaped fitting 10 is mounted in the ingress portion of the main air line or conductor 6 adjacent and downstream of the air inlet 4.

A suitable control or servo valve 13 is mounted in the main gas line 7 adjacently downstream of the gas inlet 5 for accurately regulating flow therethrough. This valve is adapted to be actuated electrically by a controller or servo 15 in such manner as to keep at a predetermined value the the electrical signal emanating from thermocouples 16, 17 connected in electrical opposition to each other and disposed within carbon monoxide flames 18, 19 of the burners 2, 3, respectively. Reference to FIG. 7 and accompanying description of the Clingman, Jr. patent is made for an illustration of the structure and operation of a suitable controller capable of actuating the gas control valve in accordance with the present invention. As will be apparent, the gas control valve 13 is actuated in such manner that the temperature difference between the burner flames 18, 19 is maintained constant; also, the air to gas ratio is always higher in burner 3 than in burner 2 due to a flow restriction orifice 30 being mounted in the air line 6. Thus, the sign of the temperature difference between the flames depends on whether the ratio of total air flow to total gas flow is richer or leaner than the flow required to maximize the temperatures of said flames. Usually, one of the thermocouples 16, 17 is set at a different position in its flame than the other flame whereby the temperature difference between said thermocouples is a constant plus the temperature difference between the flames.

As set forth in connection with the two burner embodiment (FIG. 3) of the Clingman, Jr. patent, the thermocouple temperature difference is maintained at a value corresponding to substantially maximum average temperatures of the flames by the coaction of the valve 13 and controller 15 which keeps the gas flow in that proportion which maximizes flame temperature.

A pair of forked or Y-shaped fittings 21, 23 are interposed in the main gas line 7 between its egress portion 11 and control valve 13, with the first and second arms of the upstream fitting 21 spaced from and extending downstream toward the respective first and second upstream extending arms of the downstream fitting 23. The respective first arms of the pair of fittings are connected to each other by a branch line or secondary conductor 25, while a parallel line or secondary conductor 27 joins the respective second arms of said fittings. The upstream fitting 21 divides or splits the gas flow evenly between the secondary conductors, and the downstream fitting 23 returns both streams to the egress portion 11 of the main gas line. A flow restriction orifice or capillary tube 29, 31 is mounted in each secondary conductor 25, 27, respectively, so as to maintain the same flow of gas through each conductor. For measuring the flow of gas therethrough, the secondary conductor 27 has a flowmeter 33 of the turbine type connected therein downstream of the capillary tube 31.

The forked or Y-shaped fitting 10 mounted in the large ingress portion of the main line or conductor 6 adjacent and downstream of the air inlet 4 has its arms extending downstream. One of the arms of the fitting 10 forms a part of the main air line, while the other arm communicates with a branch line or secondary conductor 12. A flow restriction orifice or capillary tube 14, 20 is connected in each conductor or line 6, 12 downstream of the Y-shaped fitting for maintaining the flow of air through conductor 12 in constant proportion of the air flow line 6. The ratio between the flow orifices or capillary tubes 14, 20 is such that only approximately 5% to 10% of the total flow of air through the air inlet passes through the secondary conductor 12. A solenoid valve 22 is mounted in the latter, downstream of its capillary tube 20, and has a pair of egress conductors 24, 26 communicating with the secondary conductors 25, 27, respectively, of the main gas line 7 downstream of the respective capillary tubes 29, 21. The solenoid valve 22 is adapted to be actuated by a controller 28, of the sequential or step type, which is electrically connected thereto and to the turbine-type flow-meter as well as to a recorder 32 which may be of the chart type.

As will be more fully described hereinafter, the controller 28 comprises a digital electronic circuit for switching the valve 22 between (to and from) two positions, for sensing the spin of the turbine of the flowmeter 33 and, at the end of each measurement cycle, transmits the ratio of air to gas for that cycle to memory. In a complete measurement cycle, the solenoid valve is placed by the controller in a first position adding air from the inlet 4 — through the secondary air conductor 12, capillary tube 20 and egress conductor 24 — to the secondary gas conductor 25. In the first position of the valve 22, the rate of spin of the turbine of the flowmeter is proportional to (G2) the flow of gas through secondary gas conductor 27. After the solenoid valve is switched to its second position by the controller 28, the flowmeter turbine 33 requires about 60 to 90 seconds to commence to spin at a steady rate.

Each time the solenoid valve is switched, starting of the next step is delayed for approximately 90 seconds. Also, approximately 90 seconds after the valve 22 switches to its first position, the controller initiates counting of the revolutions of the flowmeter turbine and, in most instances, the number of counts per revolution equals the number of turbine blades. In any event, the controller 28 measures (N1) the number of counts per second and stores this number in a suitable memory register (not shown). The number (N1) is proportional to (G2) the gas flow through secondary gas conductor 27.

Then, the controller 28 switches the solenoid valve to its second positin and waits approximately (90) seconds before commencing the count of turbine revolutions. The controller measures (N2) the number of counts per second, which is proportional to (G2 + A2) the gas flow through secondary gas conductor 27 plus the flow of air through said secondary conductor from secondary air conductor 12 by means of egress conductor 26. Then, the controller produces an output signal to the recorder 32 in proportion to (N2-N1)/(N1), thereby completing the cycle.

Preferably, the pressure drops across the solenoid valve 22, flowmeter turbine 29 and burners 2, 3 at the flow rates required for stable flames are of the order of 1 inch of water or less. The flow orifices or bores of the capillary tubes 14, 20, 29, 31 are of such diameters that the pressure drop thereacross is at least 10 psi. As a result under these conditions, the flows of fluids through capillary 14 of the main air line 6, through capillary 20 of the secondary air conductor 12 and through capillaries 29, 31 of the secondary gas conductors 25, 27 are substantially constant and independent of the position of the solenoid valve.

Since the gas flow orifices or capillary tubes 29, 31 are of the same size, the flow of gas through each of the conductors 25, 27 is equal whereby G1 equals G2 and whereby G2 is in a constant ratio to the total gas flow. To a first approximation, the flow rates through the air flow orifices or capillary tubes are proportional to the pressure differences thereacross and the pressure differences are the same for both, the upstream and downstream pressures being constant. Thus, the air flow (A2) through the secondary air conductor 12 is in a constant ratio to the total air flow, and the coaction of the servo valve 13 and controller 15 keeps the ratio of total air to total gas flow in proportion to the calorific value of the gas whereby (N2-N1)/(N1) is proportional to said calorific value.

Figure 2:
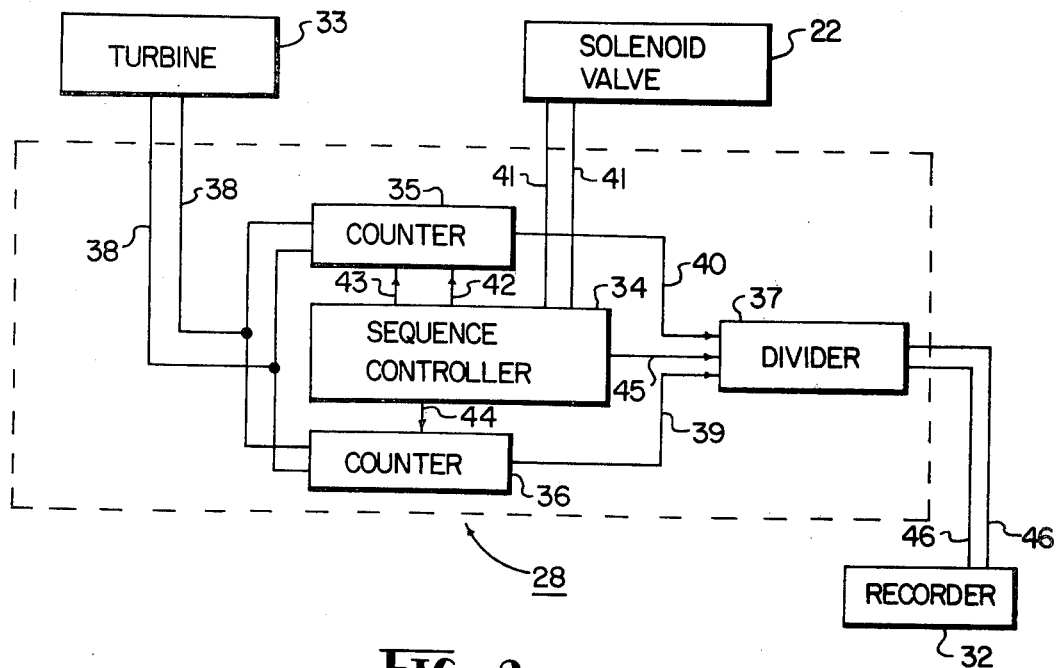
FIG. 2 is a diagrammatic view of the controller of FIG. 1.

As shown in FIG. 2, the controller 28 may comprise a sequence controller 34, a pair of counters 35, 36 connected by a pair of electrical leads 38 to the turbine flowmeter 33 of the secondary gas conductor 27, and a divider 37 connected by electrical leads 39, 40, respectively, to the counters 35, 36. A pair of electrical leads 41 connects the sequence controller 34 to the solenoid valve 22, electrical leads 42, 43 connect the first counter 35 to said sequence controller, and the latter is connected to the second counter 36 by an electrical lead 44 and to the divider 37 by an electrical lead 45. The recorder 32 is connected to the divider by a pair of electrical leads 46. A series of electrical voltage pulses is adapted to be produced by the flowmeter 33 and transmitted by the leads 38 to the first and second counters 35, 36 of the controller 28, the frequency of these pulses being in proportion to the flow of gases through said flowmeter.

The sequence controller 34 is a timing circuit which operates the solenoid valve 22 and the components of the controller 28 in accordance with the aforesaid electrical pulses. At the beginning of each cycle, no power is transmitted by leads 41 to the solenoid valve until after 90 seconds, at which time, the sequence controller activates the first counter 35 by means of a voltage signal transmitted by lead 42. This first counter records each pulse conveyed thereto by leads 38 from turbine flowmeter 33. After approximately 10 seconds, this voltage signal is removed and electrical power is applied to leads 41 so as to activate solenoid valve 22. After 90 seconds, the second counter 36 is activated by a voltage signal through lead 44. Then, the first counter 35 is reactivated in a reverse direction by a voltage signal applied through lead 43. At the end of about another 10 seconds, both counters are deactivated. The number of counts of turbine revolutions remaining on the first counter is then proportional to the air flow (A2) and the number of counts on the second counter is proportional to the gas flow (G2). Next, the lead 45 conducts a voltage pulse or signal from the sequence controller 34 to the divider 37 so as to activate the latter. Voltage pulses conducted through the respective leads 39, 40 from the first and second counters 35, 36 to the divider are in proportion to the number of counts remaining on said respective counters, and said divider produces an output signal that is in proportion to said voltage pulses conducted by said leads. This output signal is displayed by the recorder 32 and is in proportion to the calorific value. Then, the cycle of operation is repeated.

In the above description of the method of measurement the roles of combustible gas and combustion supporting gas can be reversed. That is the gas whose calorific value is to be measured can enter at 4 and the air can enter at 5. In this embodiment the calorific value would be in proportion to N1/(N2-N1), which N1 and N2 are determined as described above.

Figure 3:
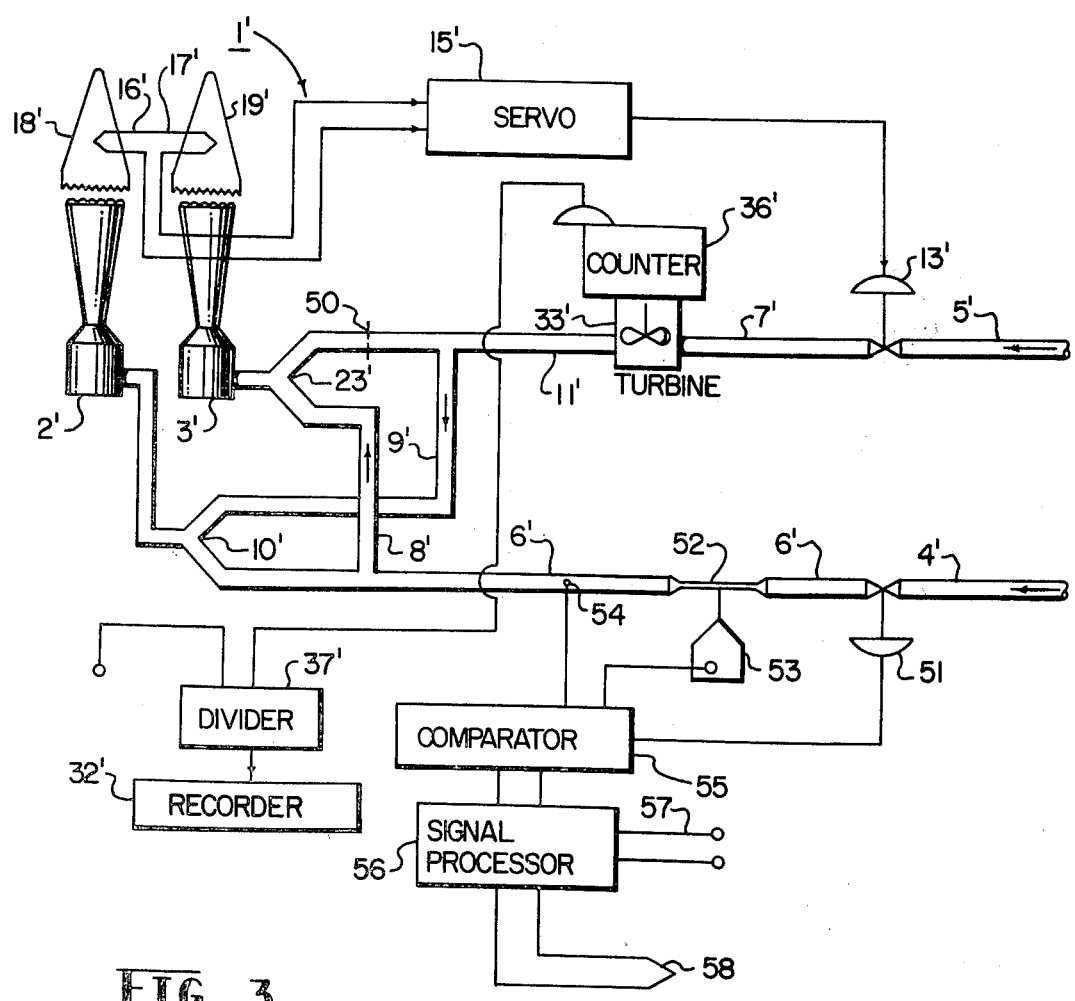
FIG. 3 is a diagrammatic view showing a modified apparatus for carrying out another method of the invention.

FIG. 3 shows an alternate embodiment of the invention; parts corresponding to those in the embodiment of FIG. 1 are given corresponding reference characters with primes (') appended. Like the embodiment of FIG. 1, that of FIG. 3 utilizes only a single flowmeter, preferably a turbine flow meter, and hence provides the same advantage of avoiding the problems of comparing measurements from two meters, each of which has its own mechanical idiosyncracies that effect accuracy of flow measurement.

In the embodiment of FIG. 3 a pair of burners 2', 3', are provided in which fuel-air mixtures are burned in a manner so that the average temperatures of the two flames are maximized, as discussed above. Air is supplied through inlet 4' to main air line 6' which delivers part of the air to the burner 2' through one of the legs of a Y-fitting 10' connected in the main air line. Gas is delivered through inlet 5' to main gas line 7' where its flow rate is measured by turbine flowmeter 33'. Egress portion 11' of the main gas line delivers a portion of the gas through one leg of a Y-fitting 23' to the burner 3' and has a branch line 9' connected to the other leg of the aforesaid Y-fitting 10' for directing the remainder of said gas to the burner 2'. Upstream of the latter fitting, a branch line 8' extends from the main air line 6' to the other leg of the aforesaid Y-fitting 23' for delivering the remainder of the air to the burner 3'. Due to this flow arrangement, separate mixtures of air and gas are provided for separate burning.

The air to gas ratio in burner 2' will always be higher than that in burner 3' by reason of a flow restriction orifice 50 in egress portion 11' in the main gas line.

Gas flow to burners 2', 3' is controlled through the loop consisting of thermocouples 16', 17', located respectively in flames 18', 19', controller or servo 15' and servo operated valve 13', substantially in the manner described above in connection with FIG. 1.

In accordance with the invention, the embodiment of FIG. 3 is provided with equipment for regulating the air flow through line 6' so that the volumetric flow rate is constant notwithstanding variations in ambient temperature and pressure, and consequent variations in the temperature and pressure of the air entering inlet 4'. This equipment includes control valve 51 in ingress portion of line 6', capillary 52 in line 6' downstream from valve 51, a pressure sensor 53 positioned to sense the pressure in capillary 52 at a selected point 53a therealong, a pressure sensor 54 downstream from capillary 52, a comparator 55, a signal processor 56, a signal input means 57 to processor 56, and a thermocouple 58, exposed to the ambient air. Signal conducting lines connect the pressure and temperature sensors and the comparator 55 and processor 56. The equipment just identified collectively comprises a constant volume flow regulator.

The regulator delivers air to the burner at a pressure substantially equal to ambient pressure.

The dimensions of capillary 52 are selected so that the air flow through it is laminar, at least from the selected point 53a to the exit end thereof. Selected point 53a is so located that the pressure drop between it and downstream pressure sensor 54 is small compared to the magnitude of the downstream pressure, which is substantially ambient.

The mode of operation of the regulator is as follows: Two inputs (voltages) are delivered to the signal processor 56. One of these is generated by thermocouple 58, and reflects the ambient temperature. The other is an externally supplied constant input (voltage), which may be conveniently provided by a selectably variable voltage source, delivered through means 57. The magnitude of the externally supplied input at 57 determines the flow rate through line 6', and in equations set forth below is designated B.

Signal processor 56 may be a simple analogue computing device of known character that multiplies the externally supplied input by the square root of the absolute temperature (represented by the thermocouple-supplied input) to produce an output or product signal which is delivered to the comparator 55. The output signal of the signal processor thus varies with variations in the ambient temperature. It varies with the externally supplied input only when the latter is deliberately changed for the purpose of changing the volume flow rate in air in line 6'.

Comparator 55, as has been pointed out, receives the output signal of signal processor 56. In accordance with the invention, it also receives pressure signals from pressure sensors 53 and 54. Comparator 55 first creates a pressure differential signal by subtracting signal 54 from signal 53. The so-created pressure differential signal is then compared in comparator 55 with the product signal from the signal processor and an output or central signal is sent from the comparator to control valve 51 for opening or closing it to bring the product signal and the pressure differential signal into equality.

The flow of fluid considerations which underlie this control arrangement for providing an automatically regulated constant volume flow rato of air are as follows: Because the flow through the capillary 52 is laminar, the volumetric flow rate, F, is given by the following expression:

$$F = \frac{A(P_1^2 - P_0^2)}{U_1 \left(\frac{T_0}{T_1}\right)^{\frac{1}{2}} P_0} \quad (1)$$

where:
A = a constant depending on dimensions of the capillary.
$U_1$ = viscosity of air at temperature $T_1$ in °K.
$T_o$ = ambient temperature in °K.
$T_1$ = a constant (selected) reference temperature in °K.
$P_1$ = pressure at sensor 53 is capillary.
$P_0$ = pressure at sensor 54 downstream of capillary.

Since, as was pointed out above $(P_1 - P_0)$ is much smaller than $P_0$, by reason of the selection of points 53 and 54, equation (1) can be rearranged as follows:

$$F = \frac{A(P_1 - P_0)[2P_0 + (P_1 - P_0)]}{U_1 \left(\frac{T_0}{T_1}\right)^{\frac{1}{2}} P_0} \quad (2)$$

Furthermore, when $P_1 - P_o = T_0 \cdot B$, as occurs in the control system as outlined above (B being the selected constant input to signal processor 56), and $(P_1 - P_0)$ is small, equation (2) can be simplified to:

$$F = \frac{2AB}{U_1 \left(\frac{1}{T_1}\right)^{\frac{1}{2}}} \quad (3)$$

all of whose terms are constants. One constant, B, is manually variable, as explained above, and the flow rate F varies directly with it.

In connection with the foregoing development of equations, it should be noted that to a first approximation, the viscosity of air varies with the square root of the temperature and is independent of the pressure, and these facts have been exploited in the control arrangement described above.

Since, in the embodiment of FIG. 3, the volumetric flow rate is constant and controlled, there is no need to measure it in the course of determining the calorific value of the gas. As has been outlined above, the servo 15' automatically adjusts the volumetric flow of gas through valve 13' so that it is in the same proportion to the constant volumetric air flow as the inverse calorific value of the gas. Gas flow alone is measured by turbine 33' and counter 36'. The signal from counter 36' is processed in divider 37' where it is converted to convenient analogue form for driving recorder 32'. The output from divider 37 is in inverse proportion to the signal from counter 36'.

In the apparatus of FIG. 3 the roles of combustion-supporting gas and combustible gas can be reversed provided the combustible gas is always of the same type so as to have the same viscosity. In this case the air would enter conduit 5' and the combustible gas would enter conduit 4'. The output from divider 37' is in proportion to the signal from counter 36'.

What is claimed is:
1. Apparatus for regulating the flow of gas through a line comprising:
   a capillary section in said line;
   a control valve in said line upstream of said capillary section;
   a first pressure sensor located at a selected point in said capillary section;
   a second pressure sensor located in said line-downstream from said capillary section;
   the dimensions of said capillary section and the location of said first pressure sensor being such that gas flow through at least that portion of the capillary section lying between the first pressure sensor and the downstream end of the section is laminar;
   a signal processor;
   means for inputting a constant signal of selected value to said processor;
   a thermocouple exposed to ambient temperature;
   said thermocouple being connected to said processor for delivering a signal thereto which is substantially proportional to the absolute ambient temperature;
   said processor including means for multiplying said constant signal by the square root of said thermocouple signal to yield a product signal;
   a comparator;
   said pressure sensors being connected to said comparator for delivering pressure magnitude signals thereto and said processor being connected to said comparator for delivering said product signal thereto;
   said comparator including means for taking the difference between said pressure magnitude signals, comparing said difference with said product signal, and sending a signal to said control valve to operate it in a direction to equalize said difference and said product signal.

* * * * *